(12) United States Patent
Kumar

(10) Patent No.: US 6,364,662 B1
(45) Date of Patent: Apr. 2, 2002

(54) DIAMOND-LIKE CARBON COATED DENTAL INSTRUMENT

(75) Inventor: Ajay Kumar, Palmdale, CA (US)

(73) Assignee: Nobel Biocare AB, Gothenburg (SE)

(*) Notice: Subject to any disclaimer, the term of this patent is extended or adjusted under 35 U.S.C. 154(b) by 0 days.

(21) Appl. No.: 09/439,247

(22) Filed: Nov. 12, 1999

Related U.S. Application Data
(60) Provisional application No. 60/129,765, filed on Apr. 15, 1999, and provisional application No. 60/108,006, filed on Nov. 12, 1998.

(51) Int. Cl.$^7$ .............................................. A61C 3/02
(52) U.S. Cl. ...................................................... 433/165
(58) Field of Search ........................................ 433/165

(56) References Cited

U.S. PATENT DOCUMENTS

| | | | |
|---|---|---|---|
| 3,971,135 A | 7/1976 | Leu | |
| 4,504,519 A | 3/1985 | Zelez | 427/39 |
| 4,560,308 A | 12/1985 | Deller | 407/53 |
| 4,681,541 A | 7/1987 | Snaper | 433/165 |
| 4,787,848 A | 11/1988 | Ross | 433/165 |
| 4,820,156 A | 4/1989 | Ross | 433/165 |
| 4,855,026 A | 8/1989 | Sioshansi | 204/192.11 |
| 4,859,493 A | 8/1989 | Lemelson | 427/45.1 |
| 4,943,236 A | 7/1990 | Linkow et al. | 433/165 |
| 4,960,643 A | 10/1990 | Lemelson | 428/408 |
| 4,987,007 A | 1/1991 | Wagal et al. | 427/53.1 |
| 5,078,605 A * | 1/1992 | Sutter et al. | 433/165 |
| 5,085,586 A | 2/1992 | Johnson | 433/224 |
| 5,096,352 A | 3/1992 | Lemelson | 411/424 |
| 5,096,418 A | 3/1992 | Coss | 433/29 |

(List continued on next page.)

FOREIGN PATENT DOCUMENTS

| | | | |
|---|---|---|---|
| GB | 966604 | 8/1964 | |
| WO | WO 93/24061 | 12/1993 | |
| WO | WO 94/20247 | 9/1994 | |

OTHER PUBLICATIONS

"Super–Slick", *Mechanical Engineering*, John DeGaspari, pp. 46–48, Apr. 1999.

"Diamond Coated Total Hip Replacements", *Clinical Orthopaedics and Relates Research*, Reijo Lappalainen, Asko Anttila and Harri Heinonen, No. 352, pp. 118–124, Jul. 1998.

"Development and Status of Diamondlike Carbon", *Synthetic Diamond: Emerging CVD Science and Technology*, A Wiley–Interscience Publication, Alfred Grill and Bernard S. Meyerson, pp. 91–96, 110–112, 121, 134–135, ®1994.

"Deposition of diamond–like carbon", *Thin Film Diamond*, Chapman & Hall, J. Robertson, pp. 107–109, ®1994.

"Atomic and Crystal Structures of Diamond", *Diamond Chemical Vapor Deposition*, Noyes Publications, Huimin Liu and David S. Dandy, pp. 8–9, ®1995.

"Raman Spectroscopy of Amorphous Carbon", *Covalently Bonded Disordered Thin–Film Materials*, Material Research Society, Symposium proceedings vol. 498, D.R. Tallant, T.A. Friedmann, N.A. Missert, M.P. Siegal, M.P. Siegal nad J.P. Sullivan, p. 37, Dec. 2–4, 1997.

Primary Examiner—Cary E. O'Connor
(74) Attorney, Agent, or Firm—Knobbe, Martens, Olson, & Bear, LLP

(57) ABSTRACT

The invention relates to a coated tool bit for a dental drilling/cutting system. The tool bit is used to prepare an osteotomy in the jawbone of a patient. The tool bit is coated with a hard carbon coating/film. The coating can comprise diamond-like carbon (DLC), amorphous diamond, crystalline diamond, or a combination thereof. The tool bit includes drilling bits, threadformers, counterbores, and cutting tips of osteotomes. Some of the advantages of the coated tool bit are reduced friction, enhanced cutting efficiency, improved heat dissipation, increased resistance to wear and corrosion, and reduced adhesion to bone, tissue and other debris.

66 Claims, 4 Drawing Sheets

U.S. PATENT DOCUMENTS

| | | | |
|---|---|---|---|
| 5,098,737 A | 3/1992 | Collins et al. | 427/53.1 |
| 5,203,804 A | 4/1993 | Nikutowski et al. | 433/8 |
| 5,261,818 A * | 11/1993 | Shaw | 433/165 |
| 5,299,937 A | 4/1994 | Gow | 433/165 |
| 5,538,423 A | 7/1996 | Coss et al. | 433/27 |
| 5,575,650 A | 11/1996 | Niznick et al. | 433/165 |
| 5,653,812 A | 8/1997 | Petrmichl et al. | 118/723 E |
| 5,681,653 A | 10/1997 | Hammond et al. | 428/336 |
| 5,725,573 A | 3/1998 | Dearnaley et al. | 623/2 |
| 5,731,045 A | 3/1998 | Dearnaley et al. | 427/527 |
| 5,747,120 A | 5/1998 | McLean, II et al. | 427/596 |
| 5,763,072 A | 6/1998 | Kato et al. | 428/336 |
| 5,763,087 A | 6/1998 | Falabella | 428/408 |
| 5,763,879 A | 6/1998 | Zimmer et al. | 250/306 |
| 5,766,394 A | 6/1998 | Anderson et al. | 156/89.11 |
| 5,772,760 A | 6/1998 | Gruen et al. | 117/104 |
| 5,792,256 A | 8/1998 | Kucherov et al. | 117/89 |
| 5,799,549 A | 9/1998 | Decker et al. | 76/104.1 |
| 5,839,897 A | 11/1998 | Bordes | 433/165 |
| 5,868,572 A | 2/1999 | Lazzara et al. | 433/173 |
| 5,997,298 A * | 12/1999 | Nowak | 433/165 |
| 6,022,350 A | 2/2000 | Ganem | 606/61 |

* cited by examiner

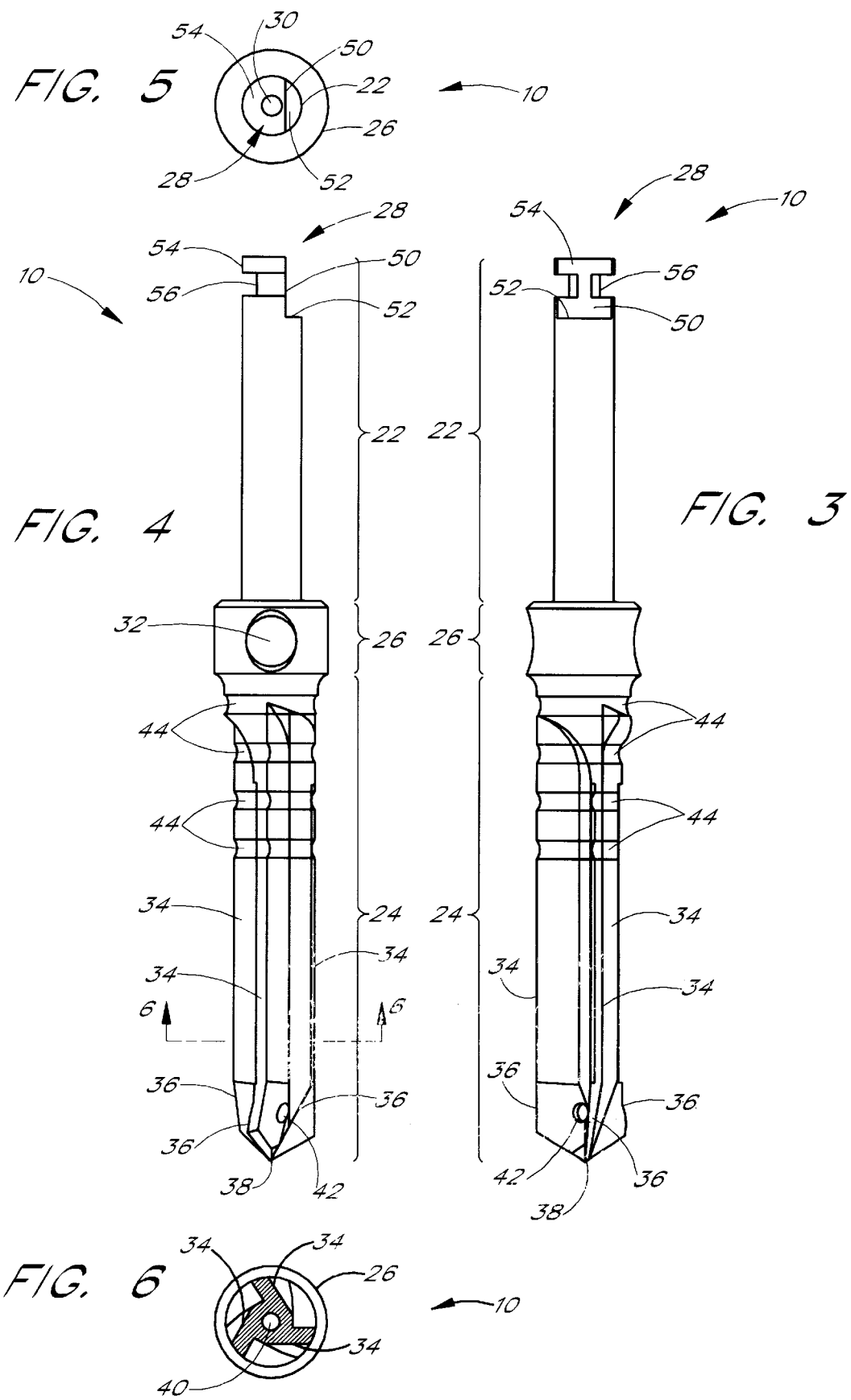

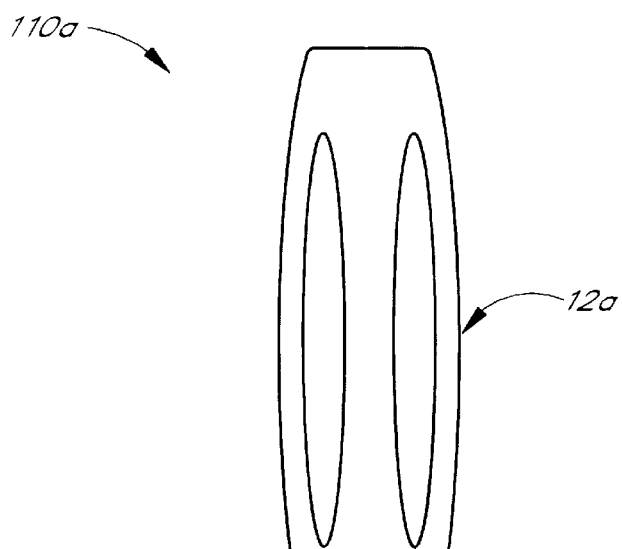
FIG. 9
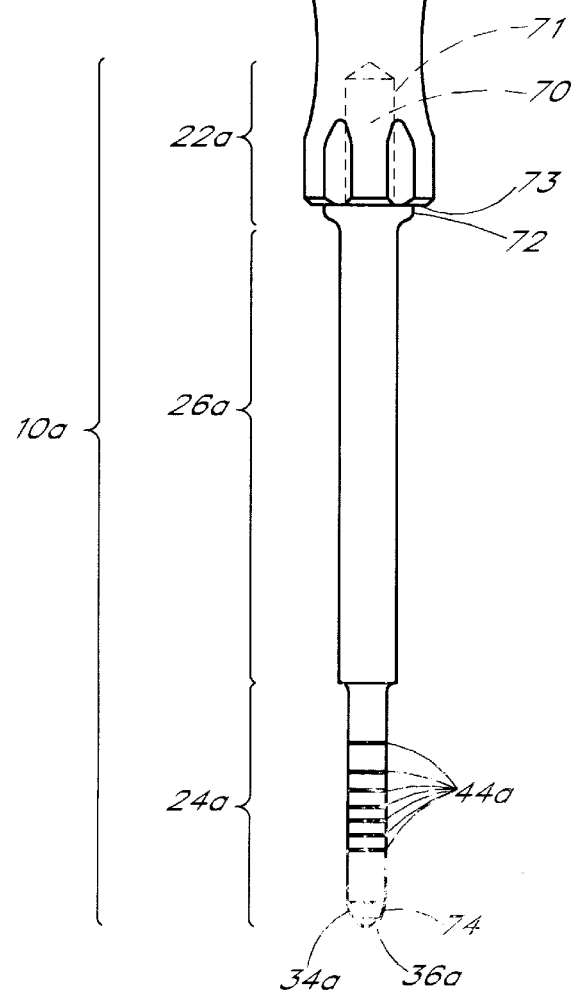
FIG. 10
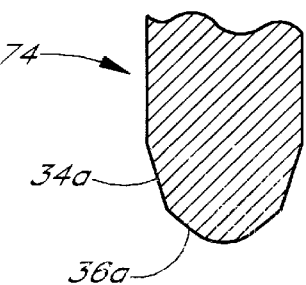

DIAMOND-LIKE CARBON COATED DENTAL INSTRUMENT

RELATED APPLICATIONS

This application claims priority to U.S. Provisional Application No. 60/108,006 filed Nov. 12, 1998 and U.S. Provisional Application No. 60/129,765 filed Apr. 15, 1999.

BACKGROUND OF THE INVENTION

1. Field of the Invention

The present invention relates generally to surgical instruments, and specifically, to tool bits, such as, drilling bits, tapping bits, cutting tips of osteotomes, and the like, for use particularly in the field of oral surgery, and more particularly in the field of dental implantology.

2. Background of the Related Art

Dental implants are surgically implanted in a patient's jawbone to provide anchors for prosthetic devices such as artificial teeth, crowns, bridges, dentures and the like. Dental implants allow people who lose their teeth to be able to comfortably smile, speak, and chew.

Typically, the dental implant that is implanted in the bone of a patient's jaw supports a socket. This socket is accessible through the overlying gum tissue for receiving and supporting one or more dental attachments or components. In turn, these components are useful to support the prosthodontic restoration.

The first step for installing an implant usually involves making an incision in the patient's gum or gingiva. Next, typically, a hole or osteotomy is formed in the jawbone of the patient. This may involve widening of a pre-existing cavity or the formation of a fresh one. The implant is then fixtured into the osteotomy. More than one osteotomy may be prepared to support a plurality of implants. Once the implant is properly secured in its subgingival position in the osteotomy a healing screw is threaded tightly over the implant.

This is followed by a healing period in which the bone is allowed to grow and surround and retain the implant. This process is called "osseointegration." The gum tissue is also allowed to heal over the implant and the healing screw. For implants in the mandible (lower jaw), healing typically requires about three months; for implants in the maxilla (upper jaw), the healing period is usually about six months.

After the osseointegration occurs and the gum has healed, the gum is reopened by making an incision in it and the healing screw is removed. A suitable healing abutment is attached to the implant. A second healing period ensues in which the gum tissue is allowed to heal around the healing abutment. Typically, this second healing period lasts from four to eight weeks.

After the second healing period, the healing abutment is removed from the implant. Typically, an impression is taken of the patient's mouth to fabricate a prosthesis or dental restoration. An abutment which supports the final restoration is attached to the implant. Lastly, the restoration is cemented or screwed to the abutment and/or implant to complete the placement of the prosthodontic restoration in the patient's mouth.

The step of forming an osteotomy typically involves drilling a hole in the patient's jawbone, utilizing one or more suitable drilling bits. This can be a difficult procedure and can cause discomfort and trauma for the patient, at least partially, due to the pain and shock involved with the penetration of a relatively large drilling bit in a person's jawbone. Drilling in high bone densities can further exacerbate and complicate the osteotomy preparation.

The high rotational drilling speeds typically involved can also generate a significant amount of heat. This is especially true since the osteotomy is not a through hole. Disadvantageously, the large amounts of heat can cause bone "necrosis" due to burning. Again, this adds to the trauma and suffering of the patient, and can inhibit the desired healing of the bone and osseointegration of the implant.

The high rotational drilling speeds can also result in high frictional forces and torques between the bone and the drilling bit. Undesirably, this increases the risk of bone fracture, and again this is detrimental to the patient. Moreover, the high frictional forces and torques may cause breakage of the drilling bit. Disadvantageously, this further complicates the procedure and adds to the trauma of the patient.

In some cases, dental counterbores are utilized to countersink the osteotomy for receiving a particularly configured implant. Also, dental threadformers may be used to thread the osteotomy for receiving a threaded implant. Both counterbores and threadformers involve removal of bone material and can cause some or all of the above-mentioned disadvantages.

In some instances, an osteotome is used to form an osteotomy in soft bone. An osteotome typically has a cutting tip that is manually manipulated by the dental practitioner to cut/compress the soft bony material. Again, the use of conventional osteotomes can suffer from some or all of the above-mentioned disadvantages.

As indicated above, it can be difficult to perform osteotomy preparing procedures efficiently, and without causing significant discomfort and trauma to the patient. Moreover, the drilling bits, counterbores, threadformers, and osteotome cutting tips are exposed to frictional forces and corrosive environments (in the patient's mouth and possibly during sterilization). As a result, in many cases, these instruments have to be replaced frequently since wear and corrosion reduce their effectiveness. Disadvantageously, this also adds to the cost of the implant procedure.

SUMMARY OF THE INVENTION

Accordingly, it is an object and advantage of the present invention to overcome some or all of these limitations by providing an amorphous hard carbon coated tool bit for a dental drilling/cutting system. In one preferred embodiment, the coating comprises diamond-like carbon (DLC). In another preferred embodiment, the coating comprises amorphous diamond. In other embodiments the coating can comprise crystalline diamond or a combination of two or more of diamond-like carbon (DLC), amorphous diamond and crystalline diamond. The tool bit preferably includes drilling bits, threadformers, counterbores, and cutting tips of osteotomes for preparing an osteotomy in a patient's jawbone. The tool bit can also include other dental cutting tools, for example, a root canal file.

Though there are a wide variety of commercially available "hard carbon" coatings, the present invention provides certain novel and unique benefits and advantages over the prior art in the field of oral surgery, and particularly in the field of dental implantology as related to the preparation of an osteotomy in a patient's jawbone. One advantage of the hard carbon coating is that it provides a reduced coefficient of friction (enhanced lubriciousness) between the tool bit and the jawbone, and desirably improves the cutting performance. Some of the other benefits and advantages arise as a consequence of the coating properties of high mechanical hardness (wear resistance), corrosion resistance, and high thermal conductivity. Some or all of these desirable properties of the hard carbon coating translate into reduced discomfort for the patient, reduced chances of accidents, bone fracture and bone necrosis, increased operational ease for the dental surgeon, saving of valuable time, and reduction in the cost of the implant procedure.

In accordance with one embodiment of the present invention, a tool bit for a dental drilling/cutting system is provided. The tool bit is adapted for preparing an osteotomy in a jawbone. The tool bit generally comprises a mounting shank and a cutting head. The mounting shank is sized and configured to interface with a handpiece of the dental drilling/cutting system. The cutting head includes a plurality of cutting edges/surfaces for rotatingly cutting bone/tissue material. A coating of hard carbon is applied on the cutting head. This greatly reduces friction and enhances the cutting performance of the tool bit.

In accordance with another embodiment of the present invention, a dental drilling bit is provided for preparing an osteotomy in a jawbone. The drilling bit generally comprises a mounting shank and a cutting head coated with an amorphous hard carbon film. The mounting shank has a chuck that is sized and configured to interface with a handpiece of a dental drilling system. The chuck has a generally I-shaped flat side and a generally semi-circular disk above and adjacent to a generally semi-circular groove. The cutting head includes a plurality of cutting edges for rotatingly removing bone material to form an osteotomy having a diameter in the range from about 1.5 mm to about 6 mm. Advantageously, the amorphous hard carbon film reduces the friction between the cutting head and bone material to enhance the cutting performance of the drilling bit.

In accordance with a further embodiment of the present invention, a dental drilling system for preparing an osteotomy is provided. The dental drilling system generally comprises a tool bit and a handpiece. The tool bit includes a cutting head for removing bone/tissue material to form an osteotomy. The handpiece holds the tool bit and is adapted to provide rotational motion to the tool bit. A coating is provided on the tool bit in the form of diamond-like carbon (DLC) for improving the cutting performance of the tool bit.

In accordance with one embodiment of the present invention, a method of forming an osteotomy using a dental drilling system is provided. The dental drilling system includes a tool bit with a cutting head that is adapted to remove bone material. The method includes the step of positioning the tool bit at a selected osteotomy site. The tool bit has a portion that is coated with amorphous hard carbon. The tool bit also has bands for indicating the depth of the osteotomy. Rotational motion is provided to the tool bit by utilizing a handpiece of the dental drilling system. The tool bit is withdrawn from the osteotomy when one of the bands indicates that the selected osteotomy depth has been reached.

In accordance with another embodiment of the present invention, a method of making a tool bit for a dental drilling system is provided. The tool bit is adapted to create an osteotomy. The method includes the step of providing a mounting shank on the tool bit. The mounting shank has a chuck at one end for interfacing with a rotation-producing handpiece of the dental drilling system. A cutting head with a plurality of cutting edges is then provided on the tool bit. An amorphous hard carbon coating is then formed on the cutting head of the tool bit. This reduces the friction between the cutting head and bone material and enhances the cutting performance of the tool bit.

In accordance with yet another embodiment of the present invention, a dental tool is provided for preparing an osteotomy in soft maxillary bone. The dental tool generally comprises a cutting tip in mechanical communication with a handle. The cutting tip includes a cutting head with a plurality of cutting surfaces for axially and rotatingly cutting/compressing the bone. The handle permits manual manipulation of the cutting tip. A film of hard carbon is applied to at least a portion of the cutting tip. Advantageously, the hard carbon film improves the lubriciousness between the cutting tip and the bone.

For purposes of summarizing the invention and the advantages achieved over the prior art, certain objects and advantages of the invention have been described herein above. Of course, it is to be understood that not necessarily all such objects and advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 3 is a front elevational view of the drilling bit of FIG. 1;

FIG. 4 is a side elevational view of the drilling bit of FIG. 1;

FIG. 5 is a top plan view of the drilling bit of FIG. 1;

FIG. 6 is a sectional view along line 6—6 of FIG. 4;

FIG. 9 is a front elevational view of an osteotome in accordance with one preferred embodiment of the present invention; and FIG. 10 is an enlarged view of one end of the cutting tip of the osteotome of FIG. 9.

DETAILED DESCRIPTION OF THE PREFERRED EMBODIMENTS

Figure 1:
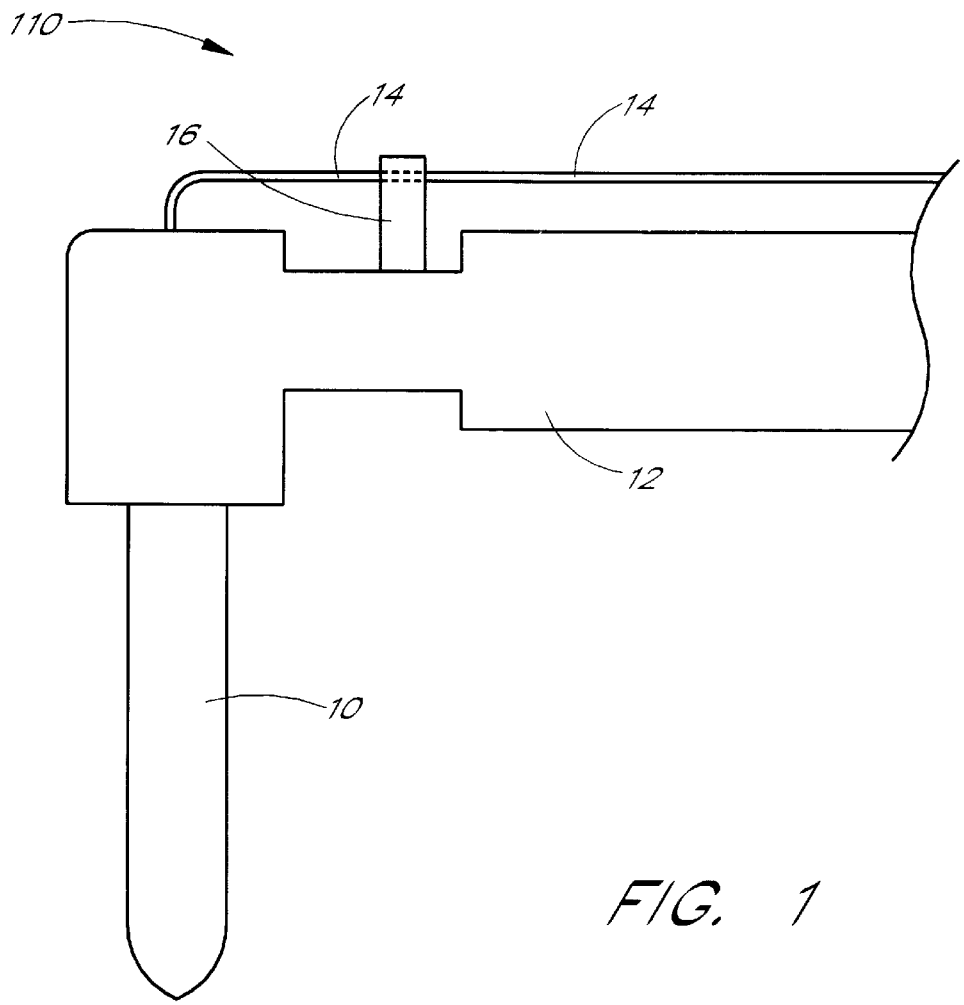
FIG. 1 is a schematic illustration of a dental drilling/cutting system in accordance with one preferred embodiment of the present invention.

FIG. 1 is a schematic illustration of a dental drilling/cutting system or apparatus 110 in accordance with one preferred embodiment. The drilling system 110 generally includes a tool bit 10 connected to a drill or handpiece 12 for providing rotor torque to the tool bit 10. The handpiece 12 may be powered by a wide variety of commercially available power sources, such as pneumatic, hydraulic or electric motors, as is known in the art. Alternatively, the tool bit 10 may be configured for hand or finger manipulation. The drilling system 110 further includes an irrigation cannula 14. The irrigation cannula 14 is supported by a support member 16 on the handpiece 12. The irrigation cannula 14 is in fluid communication with the tool bit 10 and provides fluid, for washing and cooling, as discussed in greater detail later herein.

Figure 2:
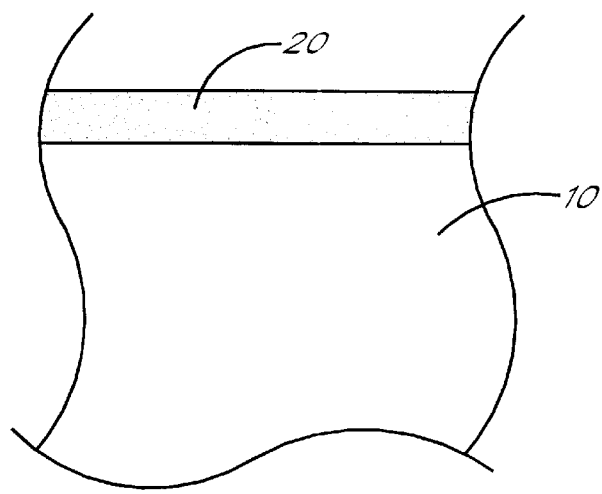
FIG. 2 is a schematic illustration of the coating (not to scale) on the tool bit of FIG. 1.

In one preferred embodiment, at least a portion of the tool bit or dental instrument 10 (FIG. 1) is coated with an amorphous hard carbon coating or film 20, as schematically illustrated in FIG. 2. The coating 20 can comprise, for example, a diamond-like carbon (DLC) coating 20, an amorphous diamond coating 20, a crystalline diamond coating 20, or a combination thereof. The coating 20 can be multi-layered and comprise one or more layers. The term "hard carbon," as used herein, can denote any or all of the above giving due consideration to achieving some or all of the benefits and advantages of the present invention.

In one preferred embodiment, the coating 20 (FIG. 2) is a diamond-like carbon (DLC) coating 20. In another preferred embodiment the coating 20 comprises an amorphous diamond coating 20. Generally, diamond-like carbon (DLC) is hydrogenated and this feature distinguishes it from amorphous diamond which has a negligible proportion of hydrogen. Both comprise an amorphous arrangement of atoms and a major or substantially sizable proportion of $sp^3$ bonding which results in high mechanical hardness, low friction, chemical inertness, more heat transfer, and other desirable properties. Diamond-like carbon (DLC) and amorphous diamond can also include some degree of $sp^2$ bonding. In general, the "hard carbon" coating 20 of the present invention comprises (a) at least some $sp^3$ bonding, (b) some, negligible or no $sp^2$ bonding, and (c) some, negligible or no hydrogenation. A discussion of $sp^n$ bonding configurations is available in many references, for example, "Synthetic Diamond: Emerging CVD Science and Technology," edited by K. E. Spear and J. P. Dismukes (sponsored by the Electrochemical Society, Inc.), Wiley, N.Y., 1994. Though there are a wide variety of commercially available "hard carbon" coatings, the present invention provides certain novel and unique benefits and advantages over the prior art in the field of oral surgery, and particularly in the field of dental implantology as related to the preparation of an osteotomy in a patient's jawbone.

As discussed in greater detail later herein, one advantage of the coating 20 (FIG. 2) is that it provides a reduced coefficient of friction (enhanced lubriciousness) between the jawbone and the hard carbon coated dental instrument of the present invention, and desirably improves the cutting performance. Some of the other benefits and advantages arise as a consequence of the coating 20 properties of high mechanical hardness (wear resistance), corrosion resistance, and high thermal conductivity. Some or all of these desirable properties of the hard carbon coating 20 translate into reduced discomfort for the patient, reduced chances of accidents, bone fracture and bone necrosis, increased operational ease for the dental surgeon, saving of valuable time, and reduction in the cost of the implant procedure.

In one preferred embodiment, and referring to FIGS. 3 to 6, the tool bit 10 (FIG. 1) is a drilling bit 10 for forming an implant-receiving osteotomy in a patient's jawbone. The drilling bit 10 generally comprises a mounting shank 22 and a cutting head 24 joined by a linking member 26. The mounting shank 22 is generally cylindrical in shape and includes a proximal end or chuck 28 which is sized and configured to be received in handpieces of conventional dental drilling systems, for example, the handpiece 12 of the dental drilling system 110 shown in FIG. 1. The chuck 28 includes a generally I-shaped flat side 50 which defines a step 52 and a generally semi-circular disk 54 above and adjacent to a generally semi-circular groove 56. Such a configuration for the chuck 28 is typically employed in the dental industry for connecting or interfacing dental tool bits to dental drills or handpieces.

In other embodiments, the mounting shank 22 and chuck 28 may be dimensioned and configured in a variety of manners with efficacy, as required or desired, giving due consideration to the goal of connecting the drilling bit 10 to a dental drilling system. The mounting shank 22 further includes a longitudinal passage 30 extending from the proximal end 28 to the linking member 26, as illustrated in FIG. 5. Preferably, the passage 30 is generally cylindrical in shape and is located substantially centrally within the mounting shank 22. The passage 30 is dimensioned and configured to accommodate the irrigation cannula 14 (FIG. 1).

Referring to FIGS. 3 to 6, the linking member 26 is generally cylindrical in shape and in mechanical communication with the mounting shank 22 and the cutting head 24. During drilling, the linking member 26 rotates along with the cutting head 24 and the mounting shank 22. The linking member 26 includes a lateral through hole 32 (FIG. 4). The hole 32 of the linking member 26 is in communication with the passage 30 of the mounting shank 22. In one preferred embodiment, the linking member 26 is also coated with a hard carbon coating, and more preferably a diamond-like carbon (DLC) coating, as schematically illustrated by the coating 20 (FIG. 2). The coating can reduce adhesion of any bone chips or other debris to the linking member 26, and thus make it easier to clean and sterilize the drilling bit 10. The coating 20 also improves the corrosion resistance of the linking member 26.

In one embodiment, the hole 32 of the linking member 26 houses an insert or plug (not shown). Preferably, the plug is fabricated from silicone. The plug includes a generally longitudinal through hole and serves to hold the irrigation cannula 14 (FIG. 1) in place and prevent undesired movement of the cannula 14 during drilling operations.

In one preferred embodiment, and referring to FIGS. 3 to 6, the cutting head 24 generally includes a plurality of flutes defining a plurality of side cutting edges 34 and terminating in a plurality of end cutting edges 36. The side cutting edges 34 extend along the length of the cutting head 24 and terminate in the end cutting edges 36. The end cutting edges terminate to define a cutting tip or end 38 of the cutting head 24. In one preferred embodiment, the cutting head 24 includes three side cutting edges 34. In one preferred embodiment, the cutting head 24 includes three end cutting edges 36. In other embodiments, as the skilled artisan will recognize, the cutting head 24 can include fewer or more side cutting edges 34 and/or end cutting edges 36, as required or desired. In one preferred embodiment, the entire cutting head 24 is coated with a hard carbon coating and more preferably with a diamond-like carbon (DLC) coating 20, as schematically illustrated by the coating 20 (FIG. 2). For example, the coating 20 may be formed by a physical vapor deposition (PVD) and/or chemical vapor deposition (CVD) technique, though other coating techniques may be utilized with efficacy, as required or desired, giving due consideration to the goal of providing a hard carbon coated dental cutting tool with improved performance.

Referring again to FIGS. 3 to 6, the cutting head 24 further includes a longitudinal passage 40 in fluid communication with a plurality of openings 42 proximate to the cutting head tip 38. The passage 40 is also in communication with the hole 32 (FIG. 4) of the linking member 26. Preferably, the passage 40 is generally cylindrical in shape and is located substantially centrally within the cutting head 24 in general alignment with the passage 30. The passage 40 is dimensioned and configured to accommodate the irrigation cannula 14 (FIG. 1). During drilling operations, the irrigation cannula 14 extends through the mounting shank passage 30, linking member hole 32 and into the cutting head passage 40, thereby rendering the irrigation cannula 14 in fluid communication with the cutting head openings 42. Thus, the irrigation cannula 14 can provide fluid during drilling operations to wash away bone debris/chips (and tissue) and to cool the drilling bit 10. Typically, a saline solution or sterile water is used as the irrigation fluid.

In one preferred embodiment, the cutting head 24 (FIGS. 3 and 4) includes three openings 42. In other embodiments, as the skilled artisan will recognize, the cutting head 24 can include fewer or more openings 42, as required or desired.

Referring to FIGS. 3 and 4, in one preferred embodiment, the cutting head 24 includes a plurality of depth indicating bands 44. The bands 44 are a visual indicator of the depth of bone penetration and are preferably distinguishable in color from the remainder of the outer surface of the cutting head 24. The bands 44 can be grooves that fully or partially circumscribe the perimeter of the cutting head 24. In one preferred embodiment, the cutting head 24 includes four depth indicating bands 44. In other embodiments, the cutting head 24 may include fewer or more bands 44, as required or desired, giving due consideration to the goal of providing generally reliable depth indicating means.

In one preferred embodiment, and referring to FIGS. 3 and 4, the depth indicating bands 44 are formed by laser etching. In other embodiments, the bands 44 may be formed by a wide variety of processes, such as chemical etching or mechanical means, as required or desired, giving due consideration to the goal of providing generally reliable depth indicating means. Preferably, the bands 44 are formed after the hard carbon coating has been applied to the dental instrument, though in alternative embodiments the bands 44 may be formed first.

Referring in particular to FIGS. 3 and 4, in one preferred embodiment, the drilling bit 10 has a length of about 38.1 mm (1.50 inches). In one preferred embodiment, the mounting shank 22 has a length of about 14.5 mm (0.57 inches), the cutting head 24 has a length of about 20.6 mm (0.81 inches), and the linking member 26 has a length of about 3.0 mm (0.12 inches). In other preferred embodiments, the drilling bit 10 may be dimensioned and configured in a wide variety of manners, as required or desired, depending on the particular nature of the osteotomy to be formed.

In one preferred embodiment, and referring to FIGS. 3 to 6, the cutting head 24 is dimensioned and configured to provide a cutting or osteotomy diameter of about 3.8 mm (0.15 inches). In another preferred embodiment, the cutting head 24 is dimensioned and configured to provide a cutting or osteotomy diameter in the range from about 1.5 mm (0.06 inches) to about 6.0 mm (0.24 inches). In one preferred embodiment, the cutting head 24 is dimensioned to form an osteotomy having sufficient depth to house dental implants (not shown) with lengths ranging from about 8 mm (0.31 inches) to about 18 mm (0.71 inches). In other preferred embodiments, the cutting head 24 may be dimensioned and configured in a wide variety of manners, as required or desired, depending on the particular nature of the osteotomy to be formed and the implant to be used.

In one preferred embodiment, the depth indicating bands 44 (FIGS. 3 and 4) have a width of about 0.76 mm (0.03 inches) and a depth of about 0.13 mm (0.005 inches) to about 0.25 mm (0.01 inches). In other preferred embodiments, the bands 44 may be dimensioned and configured in a wide variety of manners, as required or desired, giving due consideration to the goal of providing generally reliable depth indicating means.

Preferably, the drilling bit 10 (FIGS. 3 to 6) is fabricated from stainless steel, and more preferably from UNS S45500 (ASTM-A564). In one preferred embodiment, the drilling bit 10 is heat treated, electro-polished and passivated prior to the application of the coating 20 (FIG. 2). In other embodiments, the drilling bit 10 may be fabricated from a wide variety of materials, such as other metals, alloys, ceramics, plastics, as required or desired, giving due consideration to the goal of providing reduced friction and improved drilling efficiency.

The drilling bit 10 (FIGS. 3 to 6) is preferably manufactured by machining and/or grinding operations. In other embodiments, the drilling bit 10 may be manufactured by casting, forging and/or molding, among other known manufacturing technologies.

As indicated above, preferably, at least a portion of the drilling bit 10 (FIGS. 3 to 6) is coated with a diamond-like carbon (DLC) coating or film 20 (FIG. 2). In one preferred embodiment, both the cutting head 24 and the linking member 26 are coated with a diamond-like carbon (DLC) coating 20. In another preferred embodiment, only the cutting head 24 is coated with diamond-like carbon (DLC) film 20. It is preferred that the mounting shank 22 not be coated with diamond-like carbon (DLC) to maintain good frictional grip and to reduce the creation of unwanted carbon particulate matter when the mounting shank 22 is engaged with the handpiece or drill 12 (FIG. 1). In alternative embodiments, some or all of the mounting shank 22 may be coated with diamond-like carbon (DLC), as required or desired. In one embodiment, the chuck 28 of the mounting shank 22 is coated with diamond-like carbon (DLC). Advantageously, the reduced friction provided by the coating 20 on the chuck 28 facilitates in the insertion/removal of the drilling bit 10 into/from the handpiece 12.

In general, a hard carbon coating or film, such as the diamond-like carbon (DLC) coating 20 (FIG. 2), may be applied to selected surfaces of the tool bit 10 (FIG. 1) in a wide variety of configurations, as required or desired, giving due consideration to the goal of reducing friction and improving performance. As indicated above, preferably, the coating 20 is formed by a physical vapor deposition (PVD) and/or chemical vapor deposition (CVD) technique, though other coating techniques may be utilized with efficacy, as required or desired, giving due consideration to the goal of providing a hard carbon coated dental cutting tool with improved performance.

In one preferred embodiment, and referring to FIG. 2, the hard carbon coating 20 has a thickness of about 1 micron ($\mu$m). In another preferred embodiment, the hard carbon coating 20 has a thickness in the range from about 0.5 $\mu$m to about 2.0 $\mu$m. In a further preferred embodiment, the hard carbon coating 20 has a thickness in the range from about 0.5 $\mu$m to about 100 $\mu$m. In other preferred embodiments, the thickness of the hard carbon coating 20 may be selected, as required or desired, giving due consideration to the goals of providing reduced friction and improved drilling/cutting efficiency.

As indicated above, the hard carbon coating 20 (FIG. 2) comprises at least some, and preferably, a major or substantially sizable proportion of $sp^3$ chemical bonding. In one preferred embodiment, the hard carbon coating 20 comprises between about 70% to about 100% $sp^3$ bonding. In other embodiments, the coating 20 can comprise less $sp^3$ bonding, as required or desired, giving due consideration to achieving one or more of the benefits and advantages of the present invention.

Also, as indicated above, the hard carbon coating 20 (FIG. 2) in one preferred embodiment comprises diamond-like carbon (DLC) which includes some hydrogenation. In one preferred embodiment, the hydrogen content of the hard carbon or DLC coating 20 is between about 5 to about 35 atomic %. In other embodiments, the hydrogen content can be less or more, as required or desired, giving due consideration to achieving one or more of the benefits and advantages of the present invention.

In general, the present invention can be used to adjust some of the properties of the hard carbon coating 20 (FIG. 2) by varying the relative proportions of $sp^3$ and $sp^2$ bonding, and the hydrogen content. These properties can include the friction coefficient, mechanical hardness, corrosion resistance, chemical inertness, and thermal conductivity among others. In this manner, by "tweaking" the bonding and/or chemical structure of the hard carbon coating 20, it may be possible to customize the coating 20 to optimally adapt to a particular dental application by providing a synergistic balance between one or more desirable properties of the hard carbon coating 20.

In one preferred embodiment, the hard carbon coating 20 (FIG. 2) has a coefficient of friction of about 0.1. In another preferred embodiment, the hard carbon coating 20 has a coefficient of friction in the range from about 0.01 to about 0.1. In other embodiments, the hard carbon coating can have a lower or higher coefficient of friction, as needed or desired, giving due consideration to the goal of achieving one or more of the advantages of the present invention.

In one preferred embodiment, the hard carbon coating 20 (FIG. 2) has a Knoop hardness of about 2000 kg/mm$^2$. In other embodiments, the hard carbon coating 20 can have a lower or higher hardness, as needed or desired, giving due consideration to the goal of achieving one or more of the advantages of the present invention.

As indicated above, the hard carbon coating 20 (FIG. 2) can comprise a wide variety of commercially available "hard carbon" coatings including, but not being limited to, diamond-like carbon (DLC), amorphous diamond, crystalline diamond, or a combination thereof. For example, if the inclusion of a certain proportion of crystalline structure is advantageous for a particular dental application, the coating 20 may include a certain quantity of crystalline diamond along with diamond-like carbon (DLC) and/or amorphous diamond. Also, the coating 20 may be doped with small quantities of other materials to achieve a desired synergistic balance of the desirable properties of hard carbon coatings and given the goal of providing improved dental cutting tools, particularly for use in the field of dental implantology as related to the preparation of an osteotomy in a patient's jawbone.

The hard carbon coating 20 (FIG. 2) can be formed by a variety of techniques, for example, physical vapor deposition (PVD) processes and chemical vapor deposition (CVD) processes. The physical vapor deposition (PVD) may comprise single-ion beam sputtering, dual ion-beam sputtering, and radio-frequency (RF) sputtering, among others. The chemical vapor deposition (CVD) may include hot-filament CVD, plasma-assisted CVD (PACVD), direct-current (DC) PACVD, radio-frequency (RF) PACVD, direct-current (DC) thermal plasma (CVD), radio-frequency (RF) thermal plasma CVD, and flame CVD, among others.

It is desirable to clean the surface of the tool bit 10 (FIG. 1) prior to applying the coating 20 (FIG. 2). This facilitates better adherence of the hard carbon coating 20 to the passivated surface of the tool bit 10. Preferably, this cleaning process utilizes ultrasonic cleaning followed by a plasma cleaning of the tool bit 10. The plasma cleaning step includes bombardment of the tool bit 10 by suitable ions, such as argon ions. In one preferred embodiment, a combination of physical vapor deposition (PVD) and chemical vapor deposition (CVD) techniques is used to form the hard carbon coating 20 (FIG. 2) on the tool bit 10 (FIG. 1). The cleaning process and application of the coating can be performed by any one of a number of commercial coating providers.

A tool bit having features and advantages of the present invention is not limited to the particular drilling bit 10, shown in FIGS. 3 to 6, but can include a wide variety of other tool bits, such as twist drilling bits, pilot drilling bits, guide drilling bits, depth drilling bits, tapered drilling bits, among other dental drilling bits as utilized in the art, giving due consideration to the goal of reducing friction and improving drilling/cutting efficiency. As discussed in greater detail later herein, in one preferred embodiment, the tool bit comprises a cutting tip of an osteotome. The tool bit of the present invention can also comprise a root canal file as utilized in the art.

Figures 7, 8:
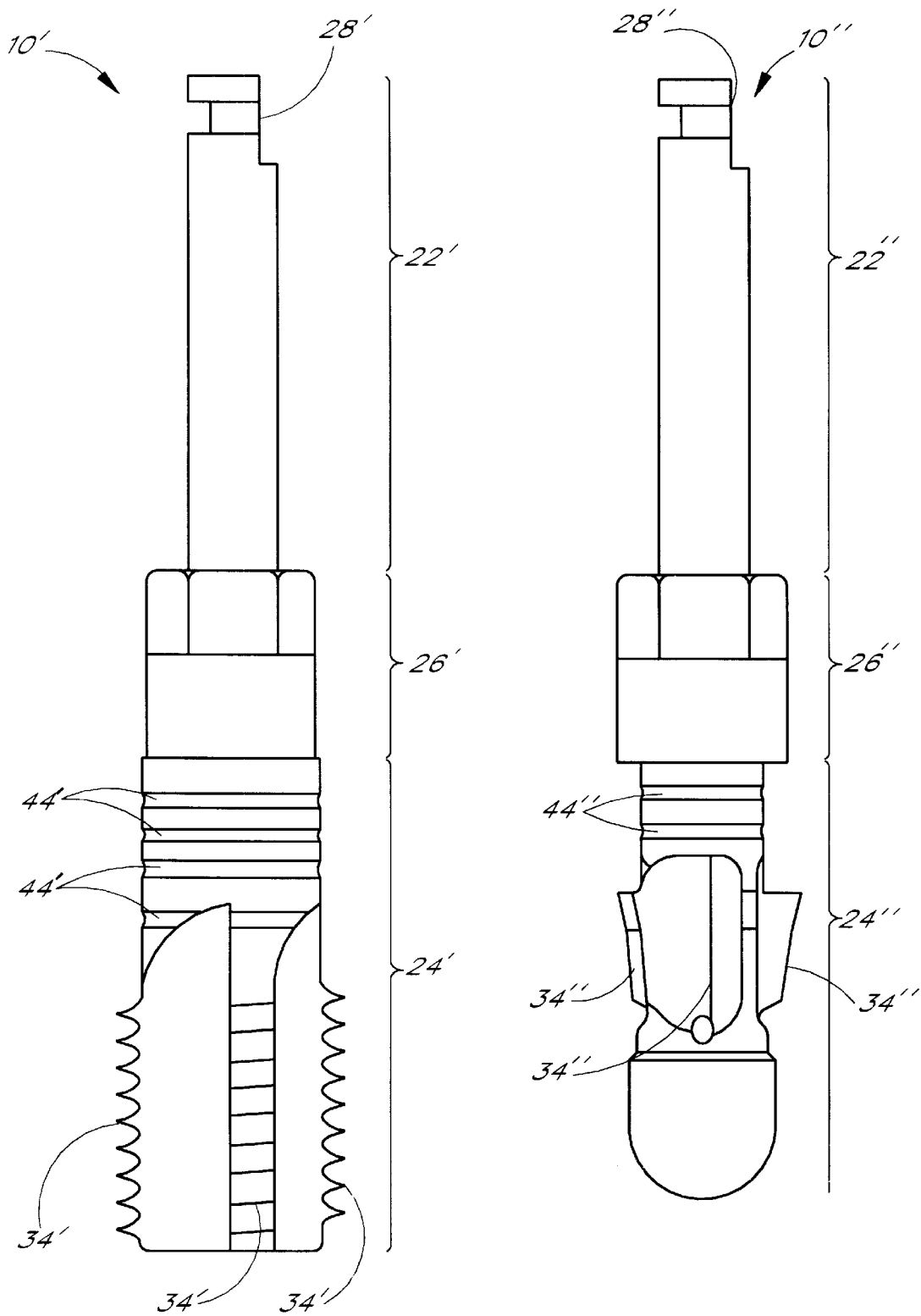
FIG. 7 is a front elevational view of the threadformer of FIG. 1.
FIG. 8 is a front elevational view of the counterbore of FIG. 1.

Additionally, in one preferred embodiment, the tool bit 10 (FIGS. 1 and 2) is a hard carbon coated dental threadformer or tapping bit 10', as illustrated in FIG. 7, for threading an osteotomy. The general use and structure of dental threadformers is known in the art. The general construction of the threadformer 10' (FIG. 7) is similar to that of the drilling bit 10 (FIGS. 3 and 4) except that the cutting/threading head 24' of the threadformer 10' is adapted to thread an osteotomy and includes cutting/threading edges 34'. Preferably, the cutting/threading head 24' of the threadformer 10' includes the hard carbon coating 20 (FIG. 2), though other portions (for example, the linking member 26' and/or the mounting shank 22') can include it also, as required or desired, giving due consideration to the goal of achieving one or more of the benefits and advantages of the present invention, such as providing reduced friction and improved performance, among other benefits and advantages. The hard carbon coating 20 (FIG. 2) in one preferred embodiment comprises diamond-like carbon (DLC), and in another preferred embodiment it includes amorphous diamond. In other embodiments, the coating 20 can comprise crystalline diamond, or a combination of two or more of diamond-like carbon (DLC), amorphous diamond, and crystalline diamond. In one preferred embodiment, the threadformer 10' (FIG. 7) includes depth indicating bands 44' (FIG. 7) which are similar to the depth indicating bands 44 shown in FIGS. 3 and 4.

In one preferred embodiment, the tool bit 10 (FIGS. 1 and 2) is a hard carbon coated dental counterbore or countersink 10", as illustrated in FIG. 8, for countersinking an osteotomy. The general use and structure of dental counterbores is known in the art. The general construction of the counterbore 10" (FIG. 8) is similar to that of the drilling bit 10 (FIGS. 3 and 4) except that the cutting/counterboring head 24" of the counterbore 10" is adapted to counterbore an osteotomy and includes cutting/counterboring edges or flutes 34". Preferably, the cutting/counterboring head 24" of the counterbore 10" includes the hard carbon coating 20 (FIG. 2), though other portions (for example, the linking member 26" and/or the mounting shank 22") can include it also, as required or desired, giving due consideration to the goal of achieving one or more of the benefits and advantages of the present invention, such as providing reduced friction and improved performance, among other benefits and advantages. The hard carbon coating 20 (FIG. 2) in one preferred embodiment comprises diamond-like carbon (DLC), and in another preferred embodiment it includes amorphous diamond. In other embodiments, the coating 20 can comprise crystalline diamond, or a combination of two or more of diamond-like carbon (DLC), amorphous diamond, and crystalline diamond. In one preferred embodiment, the counterbore 10" (FIG. 1) includes depth indicating bands 44" (FIG. 8) which are similar to the depth indicating bands 44 shown in FIGS. 3 and 4.

In general, the hard carbon coating 20 (FIG. 2) of the present invention can be applied to a wide variety of osteotomy preparation dental tools and other dental cutting tools as utilized in the art, giving due consideration to the goal of providing reduced friction, enhanced cutting performance, and other benefits and advantages.

In operation, the dental drilling system 110 (FIG. 1), including the tool bit 10 with the coating 20, the handpiece 12 and the irrigation cannula 14, is used in the preparation of one or more osteotomies in a patient's jawbone. The motorized handpiece 12 is held in the operator's hand and the tool bit 10 is positioned at the desired osteotomy site. The handpiece 12 provides rotational motion to the tool bit 10 for penetrating the patient's jawbone. The procedure can involve the use of one or more types of tool bits 10, such as twist drilling bits, pilot drilling bits, guide drilling bits, depth drilling bits, tapered drilling bits, among other dental drilling bits as utilized in the art. Typically, the procedure involves using tool bits 10 of progressively increasing size to gradually increase the size of the osteotomy. In the latter stages, depth drilling bits, such as the drilling bit 10 (FIGS. 3 and 4) with depth indicating bands 44 are utilized to finalize the size and depth of the osteotomy. During drilling the irrigation cannula 14 is used to provide fluid (typically saline solution or sterile water) to the drilling site. Typically, when drilling, an in-and-out-motion is utilized with the drilling bit 10 being periodically withdrawn from the bone to allow the irrigation fluid to wash away bone chips/debris (and tissue). The irrigation also assists in cooling the tool bit 10 and the osteotomy site. One or more osteotomies may be prepared in this manner, as dictated by the particular needs of the patient. Because of the reduced coefficient of friction, the hard carbon coated dental instrument exhibits a reduced adhesion tendency for soft tissue, thereby rendering the instrument easier to clean.

In some cases, after the drilling bits 10 (FIGS. 3 and 4) have been used to form an osteotomy, a counterbore 10" (FIG. 8) is utilized to countersink the osteotomy. This procedure may be used to prepare the osteotomy for handling a particular type of dental implant, for example, one having a larger diameter at the gingival end. Preferably, the counterbore 10" is used with the dental drilling system 110 (FIG. 1).

The osteotomy may be used to house a cylindrical implant or a threaded implant. These implants are well known in the art, and hence will not be described herein. In the case of cylindrical implants, the implant is simply pushed into the osteotomy. Similarly, for self-tapping threaded implants, the threaded implant is threaded into the osteotomy.

In the case of non-self-tapping threaded implants, a threadformer or tapping bit 10' (FIG. 7) may be used to provide threads in the osteotomy. The threaded implant is then threaded into position in the threaded osteotomy. Preferably, the threadformer 10' is used with the dental drilling system 110. The threadformer 10' can also be used manually by using a ratchet, as is well known in the art.

Typically, after the preparation of the osteotomy, the tool bit(s) 10 are sterilized. As is known in the art, the sterilization procedure may utilize autoclaving, dry heating or chemclaving. Preferably, the instruments are first cleaned of all bone chips and other debris using a needle and/or a brush. Advantageously, the hard carbon coating reduces adhesion to such debris making the instruments easier to clean and sterilize.

Osteotome

Referring to FIG. 9, in one preferred embodiment, the coated dental instrument or tool bit of the present invention comprises a hard carbon coated cutting tip 10*a* of an osteotome or dental cutting system/apparatus 110*a*. An osteotome aids in the placement of implants in soft bony material, for example, in soft maxillary bone. Osteotomes compress the bone laterally, providing a denser bony interface, rather than removing valuable bone from the surgical site.

The dental tool, osteotome or diamotome 110*a* (FIG. 9) further comprises a handle or handpiece 12*a* in mechanical communication with the cutting tip or tool 10*a*. The handle 12*a* provides a gripping/holding surface for the dental practitioner to manually manipulate the osteotome 110*a*. The cutting tip 10*a* of the osteotome 110*a* is pressed, pushed, and/or twisted in a back and forth rotating/tuning motion in the bony material to form an osteotomy. Thus, the cutting tip 10*a* axially and/or rotatingly cuts/compresses bony material. After the creation of the osteotomy, other instruments such as thread formers and counterbores, among others, may be used, as required or desired, depending on the particular nature of the osteotomy to be formed and the implant to be used.

Advantageously, the hard carbon coating 20 (FIG. 2) formed on the surface of the osteotome cutting tip 10*a* (FIG. 9) provides a low coefficient of friction between the cutting instrument 10*a* and the bony material. This improves the efficiency of the osteotomy preparation procedure and reduces the effort expended by the dental practitioner. Another benefit of the low friction (improved lubriciousness) is that it reduces the adhesion of bone/tissue and other debris to the cutting tip 10*a*. Desirably, this allows for easier cleaning and sterilization of the cutting tip 10*a* (and the osteotome 110*a*).

Referring to FIG. 9, the osteotome cutting tip 10*a* generally comprises a mounting shank 22*a* and a cutting head 24*a* joined by a linking/spacing member 26*a*. The mounting shank 22*a* includes a generally cylindrical protrusion 70 that is received in a cavity 71 of the handle 12*a* to attach the cutting tip 10*a* to the handle 12*a*. Preferably, the protrusion 70 is sized and configured to form a press fit in the cavity 71 such that a flange 72 of the mounting shank 22*a* is seated flush with a face 73 of the handle 12*a*. In other embodiments, the cutting tip 10*a* and the handle 12*a* can be attached in a wide variety of manners utilizing, for example, screws, adhesives, and the like. The cutting tip 10*a* and the handle 12*a* may also be formed as an integral unit.

The linking/spacing member 26*a* (FIG. 9) is generally cylindrical in shape. The linking member 26*a* links the cutting head 24*a* to the mounting shank 22*a*. The spacing member 26*a* also spaces the cutting head 24*a* from the handle 12*a* by a predetermined distance, as required or desired.

In one preferred embodiment, and referring to FIGS. 9 and 10, the cutting head 24a is generally cylindrical in shape and includes a distal end 74 with a flared side cutting surface 34a and a flared end cutting surface 36a. The flared side cuffing surface 34a is generally frusto-conical in shape and the flared end cutting surface 36a is generally conical in shape. In other preferred embodiments, fewer or more cutting surfaces and alternatively shaped cutting surfaces may be utilized efficaciously, as required or desired, giving due consideration to the goal of improving cutting performance.

In general, a hard carbon coating or film may be applied to selected surfaces of the osteotome cutting tip 10a in a wide variety of configurations, as required or desired, giving due consideration to the goal of reducing friction and improving performance. Preferably, the cutting head 24a (FIG. 9) of the cutting tip 10a includes the hard carbon coating 20 (FIG. 2), though other portions (for example, the linking/spacing member 26a) can include it also, as required or desired, giving due consideration to the goal of achieving one or more of the benefits and advantages of the present invention, such as providing reduced friction and improved performance, among other benefits and advantages. The hard carbon coating 20 (FIG. 2) in one preferred embodiment comprises diamond-like carbon (DLC), and in another preferred embodiment it includes amorphous diamond. In other embodiments, the coating 20 can comprise crystalline diamond, or a combination of two or more of diamond-like carbon (DLC), amorphous diamond, and crystalline diamond.

As discussed above, the hard carbon coating 20 (FIG. 2) can be formed on the cutting tip 10a (FIG. 9) by a variety of techniques, for example, physical vapor deposition (PVD) and/or chemical vapor deposition (CVD), among others. Also, as indicated above, prior to the application of the hard carbon coating the cutting tip 10a is passivated and cleaned. Prior to the passivation, preferably, the linking/spacing member 26a is glass bead blasted to provide a satin finish.

In one preferred embodiment the hard carbon coating/film 20 (FIG. 2) formed on the osteotome cutting tip 10a (FIG. 9) has a thickness of about 1 micron ($\mu$m). In another preferred embodiment, the hard carbon coating 20 has a thickness in the range from about 0.5 $\mu$m to about 2.0 $\mu$m. In a further preferred embodiment, the hard carbon coating 20 has a thickness in the range from about 0.5 $\mu$m to about 100 $\mu$m. In other preferred embodiments, the thickness of the hard carbon coating 20 may be selected, as required or desired, giving due consideration to the goals of providing reduced friction and improved cutting efficiency and performance.

Preferably, the cutting head 24a (FIG. 9) includes a plurality of depth indicating bands 44a. The bands 44a are a visual indicator of the depth of bone penetration and are preferably distinguishable in color from the remainder of the outer surface of the cutting head 24a. The bands 44a can be grooves that fully or partially circumscribe the perimeter of the cutting head 24a. In one preferred embodiment, the cutting head 24a includes seven depth indicating bands 44a. In other embodiments, the cutting head 24a may include fewer or more bands 44a, as required or desired, giving due consideration to the goal of providing generally reliable depth indicating means.

In one preferred embodiment the depth indicating bands 44a (FIG. 9) are formed by laser etching. In other embodiments, the bands 44a may be formed by a wide variety of processes, such as chemical etching or mechanical means, as required or desired, giving due consideration to the goal of providing generally reliable depth indicating means. Preferably, the bands 44a are formed after the hard carbon coating has been applied to the dental instrument, though in alternative embodiments the bands 44a may be formed first.

Referring to FIG. 9, in one preferred embodiment, the osteotome 110a has an overall length of about 165 mm (6.5 inches) and a major diameter of about 14.7 mm (0.58 inches). In other preferred embodiments, the osteotome 110a may be dimensioned and configured in a wide variety of manners, as required or desired, depending on the particular nature of the osteotomy to be formed.

In one preferred embodiment, the osteotome cutting tip 10a (FIG. 9) has a length of about 88.9 mm (3.50 inches). In one preferred embodiment, the mounting shank 22a has a length of about 14.2 mm (0.56 inches), the cutting head 24a has a length of about 25.4 mm (1.00 inches), and the linking/spacing member 26a has a length of about 49.3 mm (1.94 inches). In other preferred embodiments, the cutting tip 10a may be dimensioned and configured in a wide variety of manners, as required or desired, depending on the particular nature of the osteotomy to be formed.

Referring to FIG. 9, in one preferred embodiment, the osteotome cutting head 24a is dimensioned and configured to provide a cutting or osteotomy diameter in the range from about 1.5 mm (0.06 inches) to about 6.0 mm (0.24 inches). In one preferred embodiment, the cutting head 24a is dimensioned to form an osteotomy having sufficient depth to house dental implants (not shown) with lengths ranging from about 8 mm (0.31 inches) to about 18 mm (0.71 inches). In other preferred embodiments, the cutting head 24a may be dimensioned and configured in a wide variety of manners, as required or desired, depending on the particular nature of the osteotomy to be formed and the implant to be used.

In one preferred embodiment, the osteotome handle 12a (FIG. 9) has an overall length of about 88.9 mm (3.5 inches) and a major diameter of about 14.7 mm (0.58 inches). In other preferred embodiments, the handle 12a may be dimensioned and configured in a wide variety of manners, as required or desired, giving due consideration to the goal of providing reliable and convenient means for manipulating the osteotome.

In one preferred embodiment, the depth indicating bands 44a (FIG. 9) have a width of about 0.25 mm (0.01 inches) and a depth of about 0.08 mm (0.003 inches) to about 0.15 mm (0.006 inches). In other preferred embodiments, the bands 44a may be dimensioned and configured in a wide variety of manners, as required or desired, giving due consideration to the goal of providing generally reliable depth indicating means.

Preferably, the osteotome cutting tip 10a (FIG. 9) is fabricated from a titanium alloy, and more preferably from Ti-6Al-4V (UNS R56400—AMS4928N or AMS4967G). In other embodiments, the cutting tip 10a may be fabricated from a wide variety of materials, such as other metals, alloys, ceramics, plastics, as required or desired, giving due consideration to the goal of providing improved cutting performance.

Preferably, the osteotome handle 12a (FIG. 9) is fabricated from a titanium alloy, and more preferably from Ti-6Al-4V (UNS R56400—AMS4928N or AMS4967G). In one preferred embodiment, the handle 12a is glass bead blasted to provide a satin finish, passivated and then anodized. In other embodiments, the handle 12a may be fabricated from a wide variety of materials, such as other metals, alloys, ceramics, plastics, as required or desired, giving due consideration to the goal of providing convenient gripping/holding means.

The osteotome 110a (FIG. 9) is preferably manufactured by machining and/or grinding operations. In other embodiments, the osteotome 110a may be manufactured by casting, forging and/or molding, among other known manufacturing technologies.

Advantages

The hard carbon coated tool bit or dental instrument of the present invention demonstrates certain advantages over conventional dental tool bits. As indicated above, the hard carbon coating 20 (FIG. 2) can be a diamond-like carbon (DLC) coating, an amorphous diamond coating, a crystalline diamond coating, or a combination thereof. In one preferred embodiment, the coating 20 comprises diamond-like carbon (DLC). In another preferred embodiment, the coating comprises amorphous diamond. The present invention exploits some or all of the desirable properties of hard carbon to provide improved dental cutting tools particularly adapted to the field of dental implantology as relating to forming an osteotomy in the jawbone of a patient.

One advantage of the coating 20 (FIG. 2) is that it provides a reduced coefficient of friction (or improved lubriciousness) between the coated tool bit and the bone material and desirably increases the cutting efficiency of the tool bit(s). The reduced friction decreases the risk of bone fracture and tool bit breakage, and has several other beneficial effects. The enhanced cutting efficiency can reduce the drilling/cutting time, and thereby result in less surgery time for the patient. This not only reduces the physical discomfort of the patient, but can also reduce the monetary expense associated with the surgical procedure.

The reduced friction (improved lubriciousness) also results in less heat generation during drilling. This decreases the chances of bone "necrosis" due to burning. Another beneficial effect of the reduced friction is that it can lessen the pain and shock involved with the penetration of the dental tool bit(s) in the patient's jawbone. Also, the improved lubriciousness can reduce the rotational torque between the tool bit and the bony material. This further reduces the risk of bone fracture and tool bit breakage, and hence shields the patient from undue pain and trauma.

Also, the reduced friction (enhanced lubriciousness) permits less axial thrust and/or rotational force to be applied by the operator during drilling/cutting. This facilitates an easier osteotomy preparation process for the operator. The decrease in frictional forces between the hard carbon coated dental instrument and the bony material can also increase the operational lifetime of the instrument, and hence decrease cost.

Another benefit of the reduced friction (improved lubriciousness) as provided by the coating 20 (FIG. 2) is that it reduces the adhesion of tissue/bone to the tool bit of the present invention. Desirably, this allows for easier cleaning of the soiled tool bit(s) following a surgical procedure. Also, in the case of threadformers (tapping bits) 10' (FIG. 7), the low friction provided by the coating 20 reduces the chances of the threadformer 10' getting stuck in the osteotomy.

Advantageously, the amorphous hard carbon coating 20 (FIG. 2) provides a mechanical barrier which prevents the release of heavy metals from the stainless steel material forming the tool bit or dental instrument. It is known that stainless steel is a highly thrombogenic material because it releases chromium and nickel which can destroy enzymes and/or proteins. Also, another benefit of the coating 20 is that it exhibits minimal adhesion to proteins, and hence makes the tool bit easier to clean.

The reduced friction as provided by the coating 20 (FIG. 2) may also allow drilling, counterboring and threading speeds (RPM) that are higher than those permitted with conventional dental tool bits. Advantageously, this can make the osteotomy preparation time faster, and hence reduce the duration of the surgical procedure.

Another advantage of the coating 20 (FIG. 2) is that it has a high thermal conductivity, and hence dissipates heat at a fast rate during the drilling/cutting procedure. This better heat transfer reduces heat build-up and reduces the chances of bone "necrosis" due to burning.

Another advantage of the coating 20 (FIG. 2) is that it provides increased surface hardness to the tool bit and improves its wear resistance properties and durability. This increases the lifetime of the tool bit cutting edges, for example, the side cutting edges 34 (FIGS. 3 and 4) and the end cutting edges 36 (FIGS. 3 and 4), and hence reduces frequent replacement of the tool bit, and thus reduces cost.

Another advantage of the coating 20 (FIG. 2) is that it provides a high degree of corrosion resistance. The coated dental instrument is exposed to a corrosive environment in the patient's mouth and also during sterilization, for example, by autoclaving, dry heating or chemclaving. The coating 20 increases the lifetime and durability of the instrument, and hence reduces frequent replacement, and thus reduces cost.

Another advantage of the coating 20 (FIG. 2) is that it is chemically inert and biocompatible. This permits the tool bit to be safely used in surgical procedures involved in the preparation of an osteotomy in a patient's jawbone.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A tool bit for a dental drilling/cutting system adapted for preparing an osteotomy in a jawbone, comprising:
   a mounting shank sized and configured to interface with a handpiece of a dental drilling/cutting system;
   a cutting head including a plurality of cutting edges/surfaces for rotatingly cutting bone/tissue material; and
   a hydrogenated coating including hard carbon applied to said cutting head.

2. The tool bit of claim 1, wherein said tool bit comprises a drilling bit.

3. The tool bit of claim 1, wherein said tool bit comprises a threadformer.

4. The tool bit of claim 1, wherein said tool bit comprises a counterbore.

5. The tool bit of claim 1, wherein said tool bit comprises a cutting tip of an osteotome.

6. The tool bit of claim 1, wherein said hard carbon is amorphous.

7. The tool bit of claim 1, wherein said coating comprises diamond-like carbon (DLC).

8. The tool bit of claim 1, wherein said coating comprises amorphous diamond.

9. The tool bit of claim 1, wherein said coating comprises crystalline diamond.

10. The tool bit of claim 1, wherein said coating comprises two or more of diamond-like carbon (DLC), amorphous diamond, and crystalline diamond.

11. The tool bit of claim 1, wherein said coating comprises a major proportion of sp$^3$ bonding.

12. The tool bit of claim 1, wherein said coating has a thickness in the range from about 0.5 µm to about 100 µm.

13. The tool bit of claim 1, wherein said coating has a coefficient of friction in the range from about 0.01 to about 0.1.

14. The tool bit of claim 1, wherein said coating has a Knoop hardness of about 2000 kg/mm$^2$.

15. The tool bit of claim 1, wherein said coating is formed by physical vapor deposition (PVD) and/or chemical vapor deposition (CVD).

16. The tool bit of claim 1, wherein said cutting head includes a plurality of depth indicating bands.

17. The tool bit of claim 16, wherein said plurality of depth indicating bands is formed by laser etching.

18. The tool bit of claim 1, further comprising a linking member for connecting said cutting head and said mounting shank.

19. The tool bit of claim 18, wherein said linking member includes a hard carbon coating.

20. The tool bit of claim 1, wherein said cutting head is dimensioned and configured to form an osteotomy having a diameter in the range from about 1.5 mm to about 6 mm.

21. The tool bit of claim 1, wherein said cutting head is dimensioned to form an osteotomy having sufficient depth to house a dental implant having a length in the range from about 8 mm to about 18 mm.

22. The tool bit of claim 1, wherein said mounting shank includes a chuck comprising a generally I-shaped flat side and a generally semi-circular disk above and adjacent to a generally semi-circular groove.

23. The tool bit of claim 1, in combination with a rotation providing handpiece to form a dental drilling/cutting system.

24. The tool bit of claim 1, wherein said coating comprises between about 5 to about 35 atomic % hydrogen.

25. A dental drilling bit for preparing an osteotomy in a jawbone, comprising:
    a mounting shank including a chuck sized and configured to interface with a handpiece of a dental drilling system, said chuck including a generally I-shaped flat side and a generally semi-circular disk above and adjacent to a generally semi-circular groove;
    a cutting head including a plurality of cutting edges for rotatingly removing bone material to form an osteotomy having a diameter in the range from about 1.5 mm to about 6 mm; and
    an amorphous hydrogenated hard carbon film coated on said cuffing head for reducing the friction between said cutting head and bone material.

26. The drilling bit of claim 25, wherein said cutting head is dimensioned to form an osteotomy having sufficient depth to house a dental implant having a length in the range from about 8 mm to about 18 mm.

27. The drilling bit of claim 25, wherein said film comprises diamond-like carbon (DLC).

28. The drilling bit of claim 25, wherein said film comprises amorphous diamond.

29. The drilling bit of claim 25, wherein said film has a thickness of about 1 micron (µm).

30. The drilling bit of claim 25, wherein said film has a coefficient of friction in the range from about 0.01 to about 0.1.

31. The drilling bit of claim 25, wherein said film comprises a major proportion of sp$^3$ bonding.

32. The drilling bit of claim 25, wherein said film is formed by physical vapor deposition (PVD) and/or chemical vapor deposition (CVD).

33. The drilling bit of claim 25, wherein said cutting head includes a plurality of depth indicating bands.

34. The drilling bit of claim 25, further comprising a linking member with amorphous hard carbon film.

35. The drilling bit of claim 25, in combination with a rotation providing handpiece to form a dental drilling system.

36. The drilling bit of claim 25, wherein said film comprises between about 5 to about 35 atomic % hydrogen.

37. A dental drilling system for preparing an osteotomy, comprising:
    a tool bit including a cutting head for removing bone/tissue material to form an osteotomy;
    a handpiece for holding said tool bit and adapted to provide rotational motion to said tool bit; and
    a coating on said tool bit in the form of hydrogenated diamond-like carbon (DLC) for improving the cutting performance of said tool bit.

38. The dental drilling system of claim 37, wherein said tool bit is a drilling bit.

39. The dental drilling system of claim 37, wherein said tool bit is a tapping bit.

40. The dental drilling system of claim 37, wherein said tool bit is a countersink.

41. The dental drilling system of claim 37, wherein said diamond-like carbon (DLC) comprises between about 70% to about 100% sp$^3$ bonding.

42. The dental drilling system of claim 37, wherein said diamond-like carbon (DLC) comprises between about 5 to about 35 atomic % hydrogen.

43. The dental drilling system of claim 37, wherein said coating has a thickness between about 0.5 µm and about 2.0 µm.

44. The dental drilling system of claim 37, wherein said coating has a coefficient of friction between about 0.01 and about 0.1.

45. The dental drilling system of claim 37, wherein said coating is formed by physical vapor deposition (PVD) and/or chemical vapor deposition (CVD).

46. The dental drilling system of claim 37, wherein said cutting head includes a plurality of depth indicating bands.

47. The dental drilling system of claim 37, further including an irrigation cannula for washing and/or cooling said osteotomy and said tool bit.

48. A method of forming an osteotomy using a dental drilling system including a tool bit with a cutting head adapted to remove bone material, comprising the steps of:
    positioning a tool bit at a selected osteotomy site, said tool bit having an amorphous hydrogenated hard carbon coated portion thereof and bands for indicating the depth of the osteotomy;
    providing rotational motion to said tool bit utilizing a handpiece of a dental drilling system; and
    withdrawing said tool bit from the osteotomy when one of the bands indicates that the selected osteotomy depth has been reached.

49. The method of claim 48, wherein said hard carbon comprises between about 5 to about 35 atomic % hydrogen.

50. A method of making a tool bit for a dental drilling system adapted to create an osteotomy, comprising the steps of:
    providing a mounting shank on a tool bit so that said mounting shank has a chuck at one end for interfacing with a rotation-producing handpiece of a dental drilling system;
    providing a cutting head with a plurality of cutting edges on said tool bit; and forming an amorphous hydrogenated hard carbon film on said cutting head of said tool bit to reduce the friction between said cutting head and bone material.

51. The method of claim 50, wherein said step of forming an amorphous hydrogenated hard carbon film includes the step of physical vapor deposition (PVD).

52. The method of claim 50, wherein said step of forming an amorphous hydrogenated hard carbon film includes the step of chemical vapor deposition (CVD).

53. The method of claim 50, wherein between said steps of providing a cutting head and forming an amorphous hydrogenated hard carbon film is included the step of passivating said tool bit.

54. The method of claim 50, wherein between said steps of providing a cutting head and forming an amorphous hydrogenated hard carbon film is included the step of ultrasonically cleaning said tool bit.

55. The method of claim 50, wherein between said steps of providing a cutting head and forming an amorphous hydrogenated hard carbon film is included the step of plasma cleaning said tool bit by bombarding said tool bit with argon ions.

56. The method of claim 50, further including the step of forming a plurality of depth indicating bands on said cutting head.

57. The method of claim 56, wherein said step of forming a plurality of depth indicating bands includes the step of etching.

58. The method of claim 50, wherein said film comprises between about 5 to about 35 atomic % hydrogen.

59. A dental tool for preparing an osteotomy in soft maxillary bone, comprising:

a cutting tip including a cutting head with a plurality of cutting surfaces for axially and rotatingly cufting/compressing bone;

a handle in mechanical communication with said cutting tip and adapted to permit manual manipulation of said cutting tip; and a film including hydrogenated hard carbon applied to at least a portion of said cutting tip to improve the lubriciousness between said cutting tip and bone.

60. The dental tool of claim 59, wherein said hard carbon is amorphous.

61. The dental tool of claim 59, wherein said film comprises diamond-like carbon (DLC).

62. The dental tool of claim 59, wherein said film comprises amorphous diamond.

63. The dental tool of claim 59, wherein said film comprises two or more of diamond-like carbon (DLC), amorphous diamond, and crystalline diamond.

64. The dental tool of claim 59, wherein said film comprises a major proportion of $sp^3$ bonding.

65. The dental tool of claim 59, wherein said film has a thickness in the range from about 0.5 $\mu$m to about 100 $\mu$m.

66. The dental tool of claim 59, wherein said hard carbon comprises between about 5 to about 35 atomic % hydrogen.

* * * * *